United States Patent
Scheuermann et al.

(10) Patent No.: US 10,751,210 B2
(45) Date of Patent: Aug. 25, 2020

(54) PATELLAR TENDON BANDAGE

(71) Applicant: BAUERFEIND AG, Zeulenroda-Triebes (DE)

(72) Inventors: Rainer Scheuermann, Raisdorf (DE); Joachim Böckelmann, Kempen (DE); Hans B. Bauerfeind, Zeulenroda-Triebes (DE)

(73) Assignee: BAUERFEIND AG, Zeulenroda-Triebes (DE)

( * ) Notice: Subject to any disclaimer, the term of this patent is extended or adjusted under 35 U.S.C. 154(b) by 467 days.

(21) Appl. No.: 15/107,865

(22) PCT Filed: Dec. 18, 2014

(86) PCT No.: PCT/EP2014/078380
§ 371 (c)(1),
(2) Date: Jun. 23, 2016

(87) PCT Pub. No.: WO2015/097051
PCT Pub. Date: Jul. 2, 2015

(65) Prior Publication Data
US 2016/0324674 A1 Nov. 10, 2016

(30) Foreign Application Priority Data
Dec. 23, 2013 (DE) .......... 10 2013 022 088

(51) Int. Cl.
*A61F 13/00* (2006.01)
*A61F 5/00* (2006.01)
(Continued)

(52) U.S. Cl.
CPC .......... *A61F 5/0106* (2013.01); *A61F 5/30* (2013.01); *A61F 13/061* (2013.01); *A61F 2005/0176* (2013.01)

(58) Field of Classification Search
CPC .......... A61F 2/4657; A61F 2002/4666; A61F 2/389; A61F 2/4684; A61F 13/00068;
(Continued)

(56) References Cited

U.S. PATENT DOCUMENTS 4,287,884 A 9/1981 Applegate
5,316,547 A 5/1994 Gildersleeve
(Continued)

FOREIGN PATENT DOCUMENTS

CN 1251511 A 4/2000
CN 101721278 A 6/2010
(Continued)

OTHER PUBLICATIONS

International Search Report (in English and German) and Written Opinion of the International Searching Authority (in German) for PCT/EP2014/078380, dated Apr. 20, 2015; ISA/EP.
(Continued)

*Primary Examiner* — Kim M Lewis
(74) *Attorney, Agent, or Firm* — Stephen T. Olson; Harness, Dickey & Pierce, P.L.C.

(57) ABSTRACT

A patellar tendon bandage includes a bandage element having an inner face and an outer face and two first pressure pad bodies on the front inner face of the bandage element for building up an infra-patellar pressure. The patellar tendon bandage additionally has at least two second pressure pad bodies on the inner face of the bandage element. The two second pressure pad bodies are positioned at the sides of the two first pressure pad bodies.

16 Claims, 5 Drawing Sheets

(51) Int. Cl.
A61F 5/01 (2006.01)
A61F 5/30 (2006.01)
A61F 13/06 (2006.01)

(58) Field of Classification Search
CPC .......... A61F 2002/3895; A61F 13/0216; A61F 13/0206; A61F 13/022; A61F 17/00; A61F 2/38; A61F 2/3859; A61F 5/0125; A61F 13/00042; A61F 13/00059; A61F 13/069; A61F 2002/30616; A61F 2002/3067; A61F 2005/0167; A61F 2005/0169; A61F 2007/0056; A61F 2013/00153; A61F 2013/00174; A61F 2013/00182; A61F 5/01; A61F 5/0102; A61F 5/0111; A61F 5/013; A61F 5/028; A61F 7/10; A61F 13/00; A61F 13/00012; A61F 13/00017; A61F 13/00029; A61F 13/00034; A61F 13/00038; A61F 13/00051; A61F 13/00063; A61F 13/0203; A61F 13/0209; A61F 13/0223; A61F 13/0226; A61F 13/0266; A61F 13/06; A61F 13/061; A61F 13/08; A61F 13/085; A61F 13/10; A61F 13/101; A61F 13/15203; A61F 13/45; A61F 13/5376; A61F 13/622; A61F 15/004; A61F 2002/30079; A61F 2002/30565; A61F 2002/30589; A61F 2002/30607; A61F 2002/30668; A61F 2002/30672; A61F 2002/30772; A61F 2002/4632; A61F 2002/4658; A61F 2002/488; A61F 2002/5004; A61F 2002/507; A61F 2002/5072; A61F 2002/6818; A61F 2002/6854; A61F 2002/701; A61F 2002/741; A61F 2007/745; A61F 2002/747; A61F 2002/7635; A61F 2002/7645; A61F 2002/7818; A61F 2005/0155; A61F 2005/0176; A61F 2005/0179; A61F 2005/0188; A61F 2007/0096; A61F 2007/0244; A61F 2007/0257; A61F 2007/0266; A61F 2007/0268; A61F 2007/0273; A61F 2007/0274; A61F 2013/00238; A61F 2013/00272; A61F 2013/00289; A61F 2013/00412; A61F 2013/00497; A61F 2013/00519; A61F 2013/0054; A61F 2013/00617; A61F 2013/00846; A61F 2013/00957; A61F 2013/15243; A61F 2013/530875; A61F 2210/009; A61F 2/32; A61F 2/40; A61F 2/4202; A61F 2/64; A61F 2/68; A61F 2/70; A61F 5/0195; A61F 5/024; A61F 5/055; A61F 5/05833; A61F 5/30; A61F 5/32; A61F 5/3776; A61F 7/02; A61F 13/0485; A61F 5/0109; A61F 5/0123; A61F 5/34; A61F 5/37; A61F 13/062; A61B 5/4528; A61B 5/4509; A61B 5/6846; A61B 5/1036; A61B 5/4585; A61B 5/686; A61B 5/0031; A61B 5/076; A61B 5/6878; A61B 5/01; A61B 2562/0247; A61B 2562/0252; A61B 5/6882; A61B 5/7225; A61B 17/025; A61B 2017/0268; A61B 2090/064; A61B 2560/0406; A61B 2562/24; A61B 5/11; A61B 5/4851; A61B 17/1666; A61B 2017/00022; A61B 2017/00221; A61B 5/1032; A61B 5/1076; A61B 5/412; A61B 5/4836; A61B 5/704; A61B 5/7425; A61B 17/1325; A61B 17/1327; A61B 17/1615; A61B 17/22012; A61B 17/2202; A61B 17/24; A61B 17/3203; A61B 17/66; A61B 18/082; A61B 18/14; A61B 2017/0256; A61B 2017/22024; A61B 2017/320008; A61B 2017/320073; A61B 2017/320098; A61B 2034/2051; A61B 2034/256; A61B 2090/065; A61B 2090/306; A61B 2090/309; A61B 2090/3966; A61B 2217/005; A61B 2217/007; A61B 2560/0209; A61B 2562/02; A61B 2562/0214; A61B 2562/0219; A61B 2562/0223; A61B 2562/0261; A61B 2562/029; A61B 2562/043; A61B 2562/182; A61B 34/20; A61B 5/0008; A61B 5/0022; A61B 5/0053; A61B 5/0082; A61B 5/0084; A61B 5/0205; A61B 5/02055; A61B 5/024; A61B 5/026; A61B 5/0261; A61B 5/0531; A61B 5/055; A61B 5/06; A61B 5/0816; A61B 5/107; A61B 5/1113; A61B 5/1114; A61B 5/1115; A61B 5/1117; A61B 5/1118; A61B 5/113; A61B 5/14507; A61B 5/14539; A61B 5/14542; A61B 5/1455; A61B 5/14551; A61B 5/447; A61B 5/4571; A61B 5/4866; A61B 5/4884; A61B 5/6801; A61B 5/6828; A61B 5/683; A61B 5/6843; A61B 5/6847; A61B 5/6891; A61B 5/6892; A61B 5/7246; A61B 5/7275; A61B 5/7282; A61B 7/00; A61B 8/0875; A61B 8/58; A61B 90/36; A61B 90/37

USPC ..................... 602/26, 23; D24/190
See application file for complete search history.

(56) References Cited

U.S. PATENT DOCUMENTS

| | | | |
|---|---|---|---|
| 6,077,242 A * | 6/2000 | Falk | A61F 5/0109 |
| | | | 602/26 |
| 6,361,549 B1 * | 3/2002 | Asatourian | A61F 5/0104 |
| | | | 606/204 |
| 7,273,464 B2 * | 9/2007 | Reinhardt | A61F 13/06 |
| | | | 602/26 |
| D686,330 S * | 7/2013 | Hess | D24/190 |
| 2008/0300523 A1 * | 12/2008 | Frishberg | A61F 5/0106 |
| | | | 602/26 |
| 2011/0160631 A1 | 6/2011 | Herresthal | |
| 2011/0288611 A1 | 11/2011 | Lunau et al. | |
| 2012/0238927 A1 | 9/2012 | Chiang | |
| 2013/0338557 A1 * | 12/2013 | Hess | A61F 5/30 |
| | | | 602/26 |

FOREIGN PATENT DOCUMENTS

| | | |
|---|---|---|
| CN | 102076292 A | 5/2011 |
| DE | 4237389 A1 | 5/1994 |
| DE | 29803103 U1 | 5/1998 |
| EP | 0010389 A1 | 4/1980 |

(56) References Cited

FOREIGN PATENT DOCUMENTS

JP    H03-254744  A1   11/1991
WO    WO-2009156143  A1   12/2009

OTHER PUBLICATIONS

Chinese Office Action in parallel application CN 201480070582.9, SIPO, Beijing, dated Dec. 3, 2018, (in English).

* cited by examiner

PATELLAR TENDON BANDAGE

CROSS REFERENCE TO RELATED APPLICATIONS

This application is a U.S. National Phase Application under 35 U.S.C. 371 of International Application No. PCT/EP2014/078380 filed on Dec. 18, 2014 and published in German as WO 2015/097051 on Jul. 2, 2015. This application is based on and claims the benefit of priority from German Patent Application No. 10 2013 022 088.2 filed on Dec. 23, 2013. The entire disclosures of all of the above applications are incorporated herein by reference.

FIELD

The present invention relates to a patellar tendon bandage comprising a bandage element having an inner face and an outer face, wherein two first pressure pad bodies are provided on the front inner face to build up and infra-patellar pressure and two second pressure pad bodies are provided on the sides of the two first pressure pad bodies.

BACKGROUND

Patellar tendon bandages per se are known. A typical patellar tendon bandage, also known as a knee brace, for example, the "Kassel patellar tendon bandage," is described in DE 32 10 060 A1. Such patellar tendon bandages lead directly to a pressure of the tendon yielding beneath the patella when the bandage is placed directly beneath the patella, which thus leads to its prestress, so that patellar pain can be reduced. Such traditional patellar tendon bandages often have two protruding pressure pad heads on the inner face, which are interconnected via a narrower tapering web so that this web allows space for the patella tendon and the patella tendon can thus be situated precisely between the two pressure pad heads. The traditional patellar tendon bandages are limited to this mechanism of action.

The technical problem on which the present invention is based is to provide improved patellar tendon bandages, in particular those which have additional functions, in particular synergistic functions, when worn. The present invention relates in particular to the technical problem of providing a patellar tendon bandage, which not only leads to a prestress on the patella tendon, but also acts on other regions beneath the patella, so that there is a stabilization effect and/or further pain relief.

SUMMARY

The present invention solves the technical problem on which it is based through the subject matters of the independent claims.

In particular the present invention solves the technical problem with a patellar tendon bandage, comprising a bandage element having an inner face and an outer face and two first pressure pad bodies situated on the front inner face of the bandage element for building up an infra-patellar pressure, wherein the patellar tendon bandage additionally has at least two second pressure pad bodies on the inner face of the bandage element, wherein the two second pressure pad bodies are positioned at the sides of the two first pressure pad bodies.

The present invention provides that, two other pressure pad bodies are provided in addition to the two traditional pressure pad bodies, i.e., the two first pressure pad bodies, which are designed, for example, as interconnected pressure pad bodies by means of a web, so that a total of at least four pressure pad bodies are provided, the four pressure pad bodies preferably being arranged side by side, in particular preferably arranged approximately in a row. The arrangement of the four pressure pad bodies is thus preferably approximately horizontal, based on a patellar tendon bandage applied around a leg.

According to the invention, the two second pressure pad bodies are positioned at the sides of the two first pressure pad bodies on the inner face of the bandage element. The term "at the sides" in conjunction with the present invention relates to a patellar tendon bandage in an alignment in which it is present when the patellar tendon bandage is applied around a leg. When the patellar tendon bandage according to the invention is applied beneath the patella, then the two first pressure pad bodies are positioned beneath the patella at the right and left of the center of the patella, as is known from the prior art, where they exert a pressure on the tissue. The two second pressure pad bodies which are positioned at the sides of the two first pressure pad bodies according to the invention are thus also positioned beneath the patella when the patellar tendon bandage is applied, but are somewhat farther to the left and/or somewhat farther to the right of the center of the patella than the first two pressure pad bodies.

In a preferred embodiment, the two second pressure pad bodies are positioned on the inner face of the bandage elements, so that when the patellar tendon bandage has been applied they are positioned in the lateral region of the knee joint and act on the muscle and tendon groups running there.

It has surprisingly been found that the additional two second pressure pad bodies in the lateral region of the knee joint can activate and stimulate the muscle and tendon groups running there. It has been found that the tendons of the muscles of the "pes anserinus," for example, support the rotation, flexion and extension of the knee joint. These muscles are used with each step taken because they support the locking and opening of the biomechanical chain in the sequence of movement. Due to the sensomotor stimulus exerted by the two second pressure pad bodies, the knee joint can switch more rapidly between being locked and being unlocked. Thus, for preloading the patellar tendon, which is accomplished by the patellar tendon bandages known from the prior art, there is additionally another guidance and sensomotor stimulus function. Thus, the two second pressure pad bodies synergistically lead to a greater knee joint stability and steadiness of gait by acting synergistically with the two first pressure pad bodies, so that the functionality of the movement of the knee joint is improved at the same time.

The two second pressure pad bodies, in interaction with the bandage element above them which may be embodied as a knit fabric, for example, also result in a further stimulation of proprioceptive stimuli. A tension and relaxation and thus an additional massaging effect are achieved here with any movement of the knee between the pressure pad bodies, the bandage element situated above them and the infra-patellar tissue.

In a preferred embodiment the two first pressure pad bodies and the two second pressure pad bodies are interconnected by webs and form a one-piece pressure pad. The four pressure pad bodies are preferably arranged at least approximately on a line.

The webs between the pressure pad bodies are preferably narrower and lower than the pressure pad bodies. The one-piece pressure pad body is preferably manufactured from a single material.

DETAILED DESCRIPTION

In a preferred embodiment the two first pressure pad bodies and/or the two second pressure pad bodies are adjustable in their positions on the bandage element.

In a preferred embodiment, the two first pressure pad bodies and/or the two second pressure pad bodies are replaceable.

In one embodiment in which the two first pressure pad bodies and the two second pressure pad bodies are interconnectable by means of webs, the pressure pad is thus preferably adjustable and/or replaceable in its position on the bandage element.

In one embodiment in which the individual pressure pad bodies are not interconnected by means of webs, it is possible to provide that the individual pressure pad bodies are adjustable in their positions on the bandage element and/or are replaceable. In particular the two first pressure pad bodies are preferably adjustable on the bandage element and/or are replaceable. In particular the two first pressure pad bodies are preferably adjustable in height on the bandage element.

In a special embodiment, the invention thus provides that the height and/or flexibility of the two first pressure pad and/or the two second pressure pad bodies or the one-piece pressure pad is/are individually shapeable and adjustable to allow individual control of the pressure acting upon the infra-patellar region. This may be desirable in the context of a therapeutic program or for implementation of various prophylactic or therapeutic goals. In a special embodiment the invention provides in particular that the height of the two first pressure pad bodies and/or of the two second pressure pad bodies or the one-piece pressure pad is individually adjustable. The invention therefore provides, for example, that the pressure pad bodies according to the invention or the one-piece pressure pad is/are detachably connected to the bandage element and can be removed from it for the purpose of adjustment or adaptation of the height or the material properties, in particular the flexibility, i.e., the Shore hardness, i.e., the pressure pad bodies or the one-piece pressure pad is/are removable and then reinsertable. In a simple height adjustment, it is not necessary to replace the pressure pad bodies or the pressure pad. It is preferably provided that the two first pressure pad bodies and/or the two second pressure pad bodies are replaceable for adjusting the effect of the pressure pad bodies on the infra-patellar region, in particular that pressure pad bodies of different heights, sizes or other mechanical properties can be inserted. This may of course also be achieved by the replaceability of the one-piece pressure pad.

Regarding the adjustability and/or replaceability, the pressure pad bodies or the pressure pad may be connected to the inner face of the bandage element via a hook-and-loop closure.

The two first pressure pad bodies and/or the two second pressure pad bodies may have any suitable form with which those skilled in the art are familiar. The pressure pad bodies are preferably pressure pad heads. The first two pressure pad bodies are preferably pressure pad heads. The second two pressure pad bodies are preferably pressure pad heads.

The pressure pad bodies may have a round or oval cross section, for example. In particular the pressure pad bodies may have an approximately hemispherical shape, for example, a hemispherical or semioval shape. However other shapes are also conceivable of course, for example, the pressure pad bodies may have a pyramid shape, a cube shape, a box shape, a polyhedral shape, a toroidal shape, a hollow cylindrical shape, a circular cylindrical shape, a conical shape or a prism shape.

The two first pressure pad bodies and/or the two second pressure pad bodies or the one-piece pressure pad is/are preferably made of a permanently elastic material, in particular silicone rubber or polyurethane but the invention is not limited to these materials. Those skilled in the art will also be familiar with suitable materials. In particular the physical mechanical behavior of the material, especially the elastic modulus is adapted to the soft tissue of the knee joint.

In a preferred embodiment, the two first pressure pad bodies and/or the two second pressure pad bodies have elevations or depressions, but elevations are preferred. The elevations are preferably nub-shaped. The pressure pad bodies thus preferably have a plurality of nubs. A pressure pad body preferably has between 2 and 20 nubs. The nubs are preferably made of the same material as the pressure pad bodies.

The bandage element is preferably designed in strips and/or as a ribbon or as a band. The bandage element is preferably designed primarily as a knitted or crocheted material.

The bandage element is preferably a band strip or a belt, wherein the band or the belt may be wrapped in the shape of a ring around a leg and then secured by means of at least one closure element. Preferably two closure elements are provided. The closure elements are preferably designed so that they allow the patellar tendon bandage to be tightened on the leg.

A preferred closure element has a deflecting eye and a hook-and-loop closure. The hoop and loop closure may be passed through the deflecting eye to close it and the bandage element thereby tightened against the leg, and this position can be secured by closing the hook-and-loop closure with another part of the bandage element.

In a preferred embodiment, the bandage element has a front function element and a fixation element, in particular a fixation belt. In a preferred embodiment, the fixation element is fastened on at least one end region of the function element by means of a fastening element, so that it is adjustable in length.

The function element in this embodiment serves as a carrier for the pressure pad or the pressure pad bodies. The fixation element serves to tighten the function element on the leg and to press the pressure pad bodies against the infra-patellar region in this way.

The function element preferably consists of a crocheted material. The fixation element is preferably made of a knitted or crocheted material or some other suitable material component. The fixation element is especially preferably made of a knitted material.

In a preferred embodiment, the at least one fastening element is fastened onto the function element on the outer face of the function element.

In a preferred embodiment the at least one fastening element is fastened onto the function element in the region of one of the two second pressure pad bodies.

In a preferred embodiment the fixation element is fastened to the two end regions of the function element by means of a fastening element so that it is adjustable in length. The two fastening elements are preferably fastened to the function element on the outer face of the function element, wherein a fastening element is fastened in the region of one of the two second pressure pad bodies.

In a preferred embodiment the fixation element has at least one hook-and-loop closure. In a preferred embodiment, the at least one fastening element has a deflecting eye.

In a preferred embodiment the fixation element has two hook-and-loop closures on the ends. In a preferred embodiment, the function element has two deflecting eyes in particular on its outer face. In such an embodiment, the fixation element is thus fastened on the function element by means of two hook-and-loop closures, each of which can be pulled through one of the two deflecting eyes and can then be secured on the fixation element by means of the hook-and-loop closure. Therefore, the desired adjustment in length of the patellar tendon bandage is possible by a simple method.

In a preferred embodiment, the patellar tendon bandage thus has a front function element and a fixation element, wherein the fixation element is fastened onto the two end regions of the function element by means of one fastening element each in a manner that allows adjustment of length, and wherein the first fastening element is positioned in the region of the one second pressure pad body, and the second fastening element is positioned in the region of the other second pressure pad body. The two fastening elements are preferably positioned on the outer face of the bandage element, in particular the function element.

This preferred embodiment leads to an additional technical advantage namely that the two fastening elements can serve as pressure application points of the fixation belt directly on the two second pressure pads. Due to the preferred positioning, the stress transferred through the fixation element is transferred exactly to the position of the function element where the two second pressure pads are situated. This advantageously achieves the result that the two second pressure pad bodies absorb from the fastening elements the pressure that is transferred from the fixation element to the two fastening elements. A particularly good pressure effect of the two second pressure pad bodies on the infra-patellar region can be achieved in this way.

The present invention also relates to a patellar tendon pressure pad, comprising four pressure pad bodies arranged almost on a line and interconnected by means of webs.

Preferred embodiments of the patellar tendon pressure pads according to the invention are derived from the embodiments of the pressure pad bodies and/or pressure pads as described above.

A patellar tendon pressure pad according to the invention is suitable in particular as an element for equipping a patellar tendon bandage.

The subject matter of the invention is also a patellar tendon bandage which contains the patellar tendon pressure pad according to the invention. This may be designed in particular as a crocheted orthotic apparatus with an inserted patellar tendon pressure pad according to the invention.

The present invention also relates to a patellar tendon bandage according to the invention or a patellar tendon pressure pad according to the invention for pain relief, in particular in anterior knee pain. Such anterior knee pain may be caused by, for example, a patellar apex syndrome, by a chondropathy patella condition, by a femoro-patellar arthrosis, by a cruciate ligament insufficiency of the anterior cruciate ligament, by a quadricep paresis or by a muscular dystrophy. Use in post-operative or post-traumatic rehabilitation training is also possible. The invention relates accordingly to such applications of the patellar tendon bandage according to the invention or the patellar tendon pressure pad according to the invention.

The subject matter of the invention is also prophylactic and/or therapeutic use of the patellar tendon bandage according to the invention or the patellar tendon pressure pad according to the invention for treatment of anterior knee pain syndrome.

The invention also relates to a patellar tendon bandage according to the invention or a patellar tendon pressure pad according to the invention for a corresponding prophylactic and/or therapeutic use.

The invention is described in greater detail below on the basis of the following figures although the embodiments of the invention presented there are not to be understood in a restrictive form.

Figure 1:
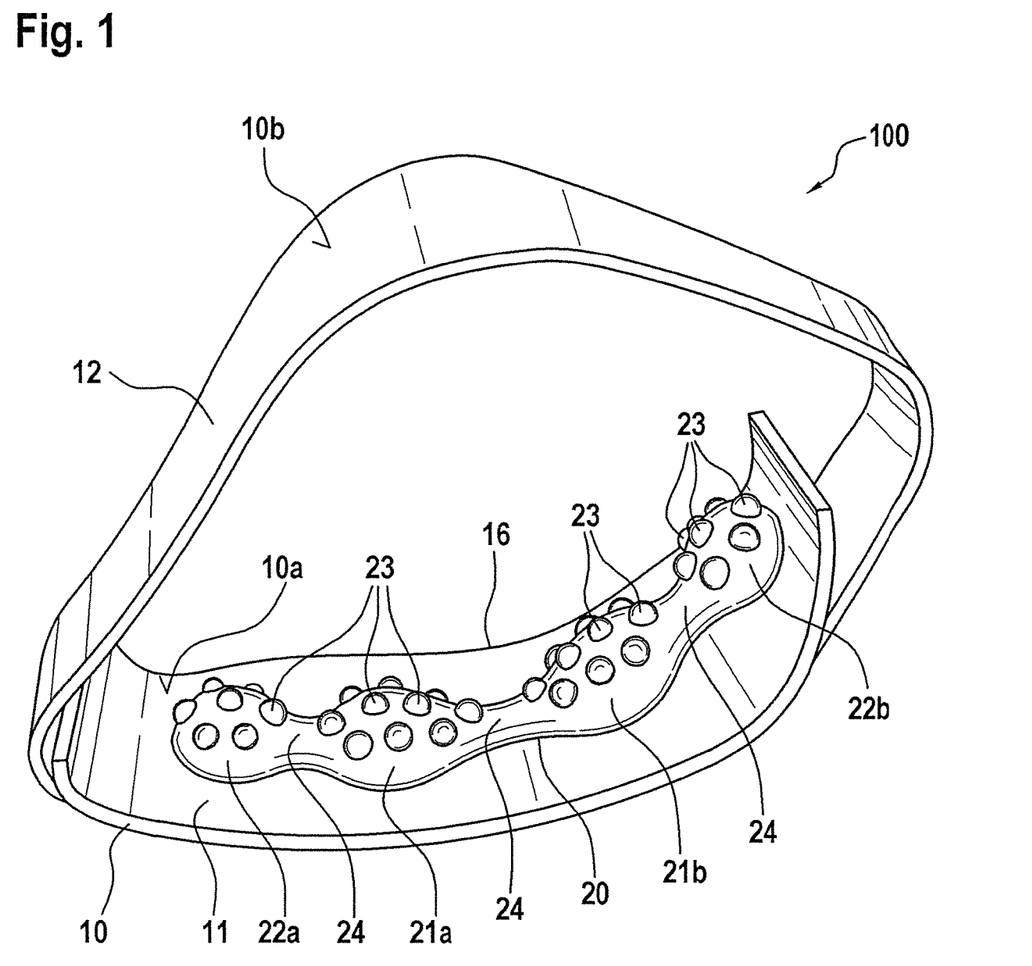
FIG. 1 shows a side view of a preferred embodiment of the patellar tendon bandage according to the invention.

FIG. 1 shows a preferred embodiment of the patellar tendon bandage (100) according to the invention in a side view. The patellar tendon bandage (100) comprises a bandage element (10) having a function element (11) and a fixation element in the form of a fixation belt (12). The bandage element (10) has an inner face (10*a*) and an outer face (10*b*). The function element (11) forms the front side of the bandage element (10) and is worn below the patella. There is a recess (16) for the patella in the upper region of the function element (11). The function element (11) may be formed from a knitted material, for example, and the fixation element (12) may be formed from a knitted or crocheted material.

On the inner face (10*a*) of the function element (11) a pressure pad (20) is positioned. The pressure pad has two first pressure pad bodies in the form of pressure pad heads (21*a*, 21*b*) with an oval cross section and two second pressure pad heads in the form of pressure pad heads (22*a*, 22*b*) with an approximately round cross section. The two second pressure pad heads (22*a*, 22*b*) are positioned at the sides of the two first pressure pad heads (21*a*, 21*b*). The total of four pressure pad heads (22*a*, 21*a*, 21*b*, 22*b*) are connected to one another by means of webs (24) and thus for the one piece pressure pad (20). When the patellar tendon bandage according to the invention is applied beneath the patella, the two first pressure pad bodies are positioned beneath the patella, at the right and left of the center of the patella, where they exert a pressure on the tissue, as is known from the prior art. The two second pressure pad bodies, which are positioned at the sides of the two first pressure pad bodies according to the invention, are thus also positioned beneath the patella with the patellar tendon bandage applied but are somewhat further to the left and/or somewhat further to the right of the center of the patella than the first two pressure pad bodies. Due to the design of the pressure pad bodies according to the invention, the advantageous effect presented in the description is achieved when wearing the patellar tendon bandage (100) beneath the patella.

The four pressure pad heads (22*a*, 21*a*, 21*b*, 22*b*) each have a plurality of elevation in the form of nubs (23). This leads to an additional advantageous massaging effect and transfer of stimulation through all four pressure pad heads (22a, 21a, 21b, 22b).

Figure 2:
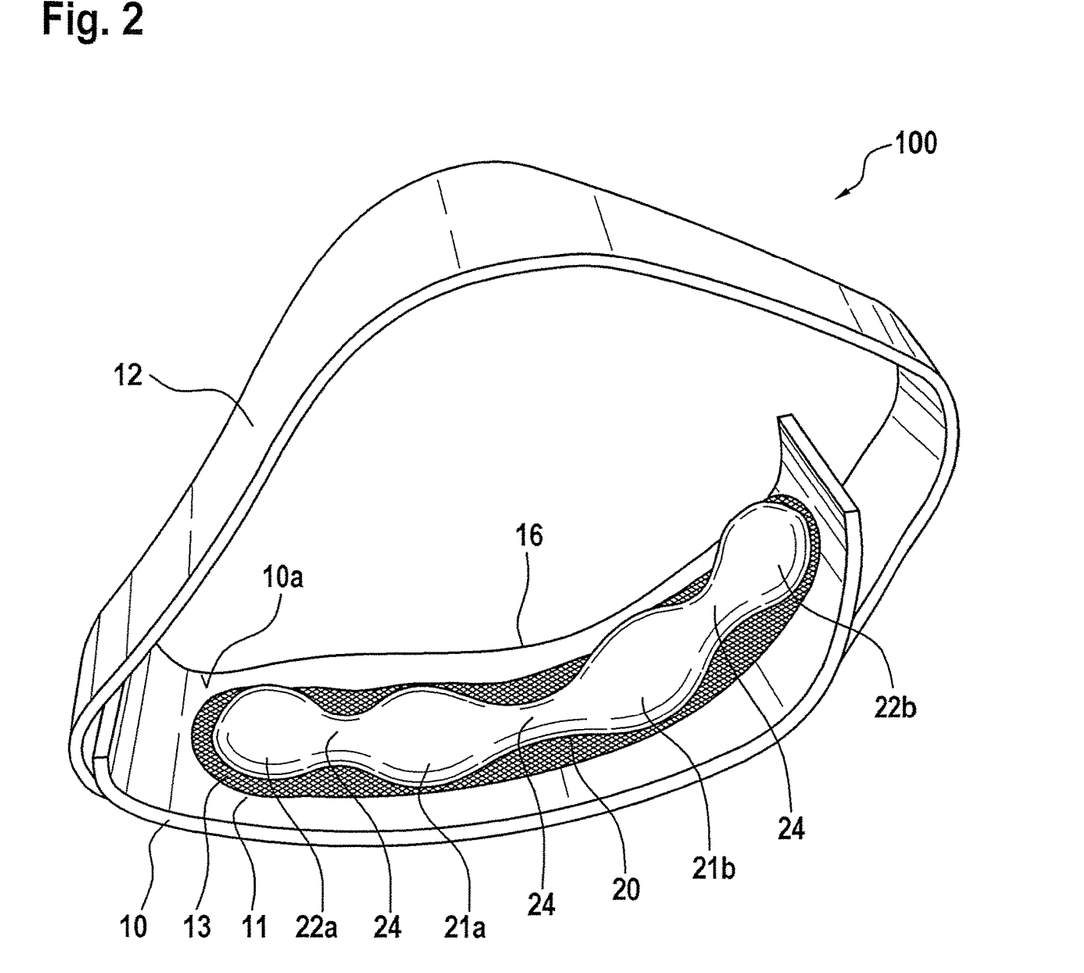
FIG. 2 shows a side view of another preferred embodiment of the patellar tendon bandage according to the invention.
Figure 4:
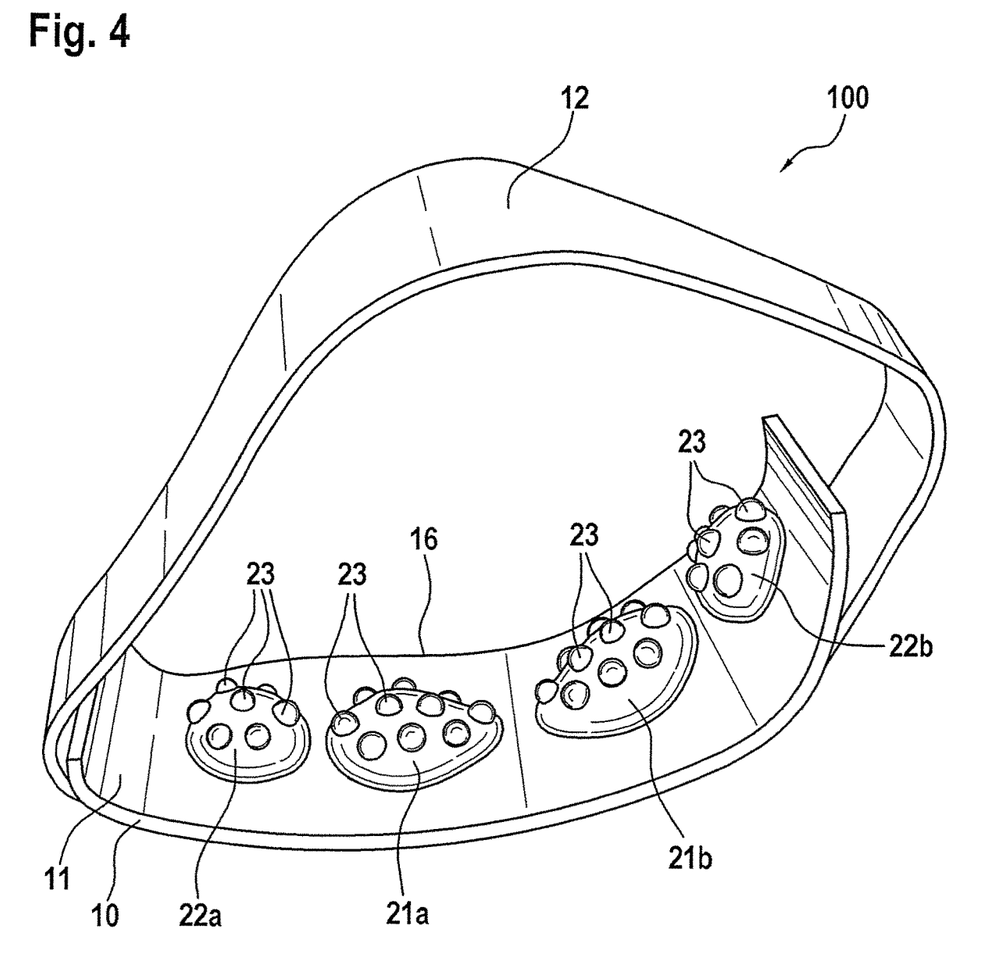
FIG. 4 shows a side view of another preferred embodiment of the patellar tendon bandage according to the invention.

Additional possible embodiments can also be derived from FIGS. 2 and 4 for those skilled in the art.

FIG. 2 shows an alternative embodiment of the patellar tendon bandage (100) according to the invention in a side view. As shown in FIG. 1, the patellar tendon bandage (100) again comprises the bandage element (10) with a function element (11) having the recess (16) and a fixation element in the form of a fixation belt (12).

A pressure pad (20) is positioned on the inner face (10a) of the function element (11). It again has two first pressure pad heads in the form of pressure pad heads (21a, 21b) having an oval cross section and two second pressure pad heads in the form of pressure pad heads (22a, 22b) having an approximately round cross section. The two second pressure pad heads (22a, 22b) are positioned at the sides of the two first pressure pad heads (21a, 21b). The total of four pressure pad heads (22a, 21a, 21b, 22b) are connected to one another by means of webs (24) and thus form the one-piece pressure pad (20).

The pressure pad (20) is reversibly connected to the function element (11) by means of a hook-and-loop closure (13) and may thus be adjusted in their position, for example, in height with respect to the function element (11) or replaced by a different pressure pad.

Figure 3:
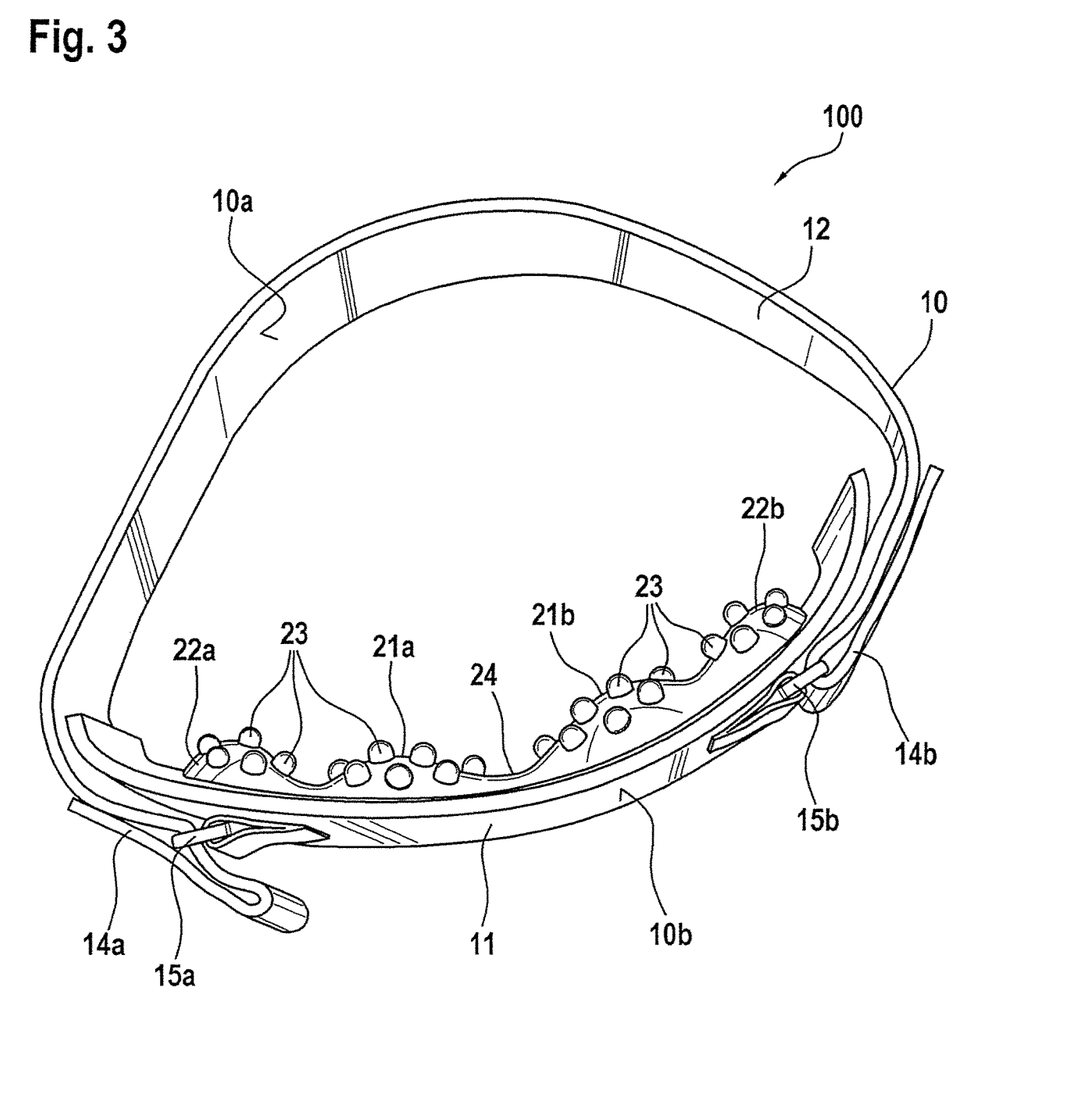
FIG. 3 shows an oblique view of the patellar tendon bandage from FIG. 1.

Those skilled in the art can also deduce additional possible embodiments from FIGS. 1 and 3 to 4.

FIG. 3 shows the patellar tendon bandage (100) from FIG. 1 in an oblique view. The bandage element (10) can be seen with the inner face (10a) and outer face (10b) with the function element (11) and the fixation element in the form of a fixation belt (12). The pressure pad (20) with the four pressure pad heads (22a, 21a, 21b, 22b) that are interconnected by means of webs (24) and have nubs (23) is also shown.

Each of the two ends of the fixation belt (12) are reversibly connected to an end region of the function element (11) in order to form the ring-shaped bandage (100). The two reversible and longitudinally adjustable connections between the fixation belt (12) and the function element are made possible by two hook-and-loop closures (14a, 14b) on the fixation belt (12) and two deflecting eyes (15a, 15b) on the function element (11), through which the fixation belt (12) is pulled in the region of the hook-and-loop closures (14a, 14b). This permits simple tightening and securing of the patellar tendon bandage (100) on a leg.

The two deflecting eyes (15a, 15b) are positioned on the outer face (10b) of the function element (11), precisely where the two second pressure pad heads (22a, 22b) are positioned on the inner face (10a) of the function element (11). The forces created by the fixation belt (12) are therefore advantageously transferred directly via the first deflecting eye (15a) to the first of the second pressure pad heads (22a) and via the second deflecting eye (15b) directly to the second of the second pressure pad heads (22b). This advantageously achieves the result that the two second pressure pad heads (22a, 22b) receive this pressure directly from the deflecting eyes (15a, 15b) and transfer it as pressure to the leg. This permits a particularly good pressure effect of the two second pressure pad heads (22a, 22b) on the infra-patellar region.

Those skilled in the art can also derive additional possible embodiments from FIGS. 2 and 4.

FIG. 4 shows another embodiment of the patellar tendon bandage (100) according to the invention in a side view. The patellar tendon bandage (100) again comprises the bandage element (10) with a function element (11) together with the recess (16) and a fixation element in the form of a fixation belt (12).

Two first pressure pad bodies in the form of pressure pad heads (21a, 21b) with an oval cross section and two second pressure pad heads in the form of pressure pad heads (22a, 22b) within an approximately round cross section are positioned on the inner face (10a) of the function element (11). The two second pressure pad heads (22a, 22b) are again positioned at the sides of the two first pressure pad heads (21a, 21b). The total of four pressure pad heads (22a, 21a, 21b, 22b) are not interconnected here by means of webs and thus do not form a one-piece pressure pad. The four pressure pad heads (22a, 21a, 21b, 22b) each have a plurality of elevations in the form of nubs (23).

The four pressure pads (22a, 21a, 21b, 22b) can be reversibly connected to the function element (11) by means of a hook-and-loop closure, for example, and may thus be adjusted in their position, for example, in height with respect to the function element (11) or may be replaced by another pressure pad. Alternatively, however, it is also possible to provide that the four pressure pad heads (22a, 21a, 21b, 22b) are fixedly connected to the function element (11).

Those skilled in the art can also derive additional possible embodiments from FIGS. 1 to 3.

FIG. 5 shows two different embodiments of the patellar tendon pressure pad (20) according to the invention.

The patellar tendon pressure pad (20) in FIG. 5 has two first pressure pad bodies in the form of pressure pad heads (21a, 21b) with an oval cross section and two second pressure pad bodies in the form of pressure pad heads (22a, 22b) having an approximately round cross section. The two second pressure pad heads (22a, 22b) are positioned at the sides of the first two pressure pad heads (21a, 21b). The total of four pressure pads heads (22a, 21a, 21b, 22b) are interconnected by means of webs (24), which taper in the middle and thus form the one-piece pressure pad (20). The four pressure pad heads (22a, 21a, 21b, 22b) each have a plurality of elevations in the form of nubs (23).

Figure 5A:
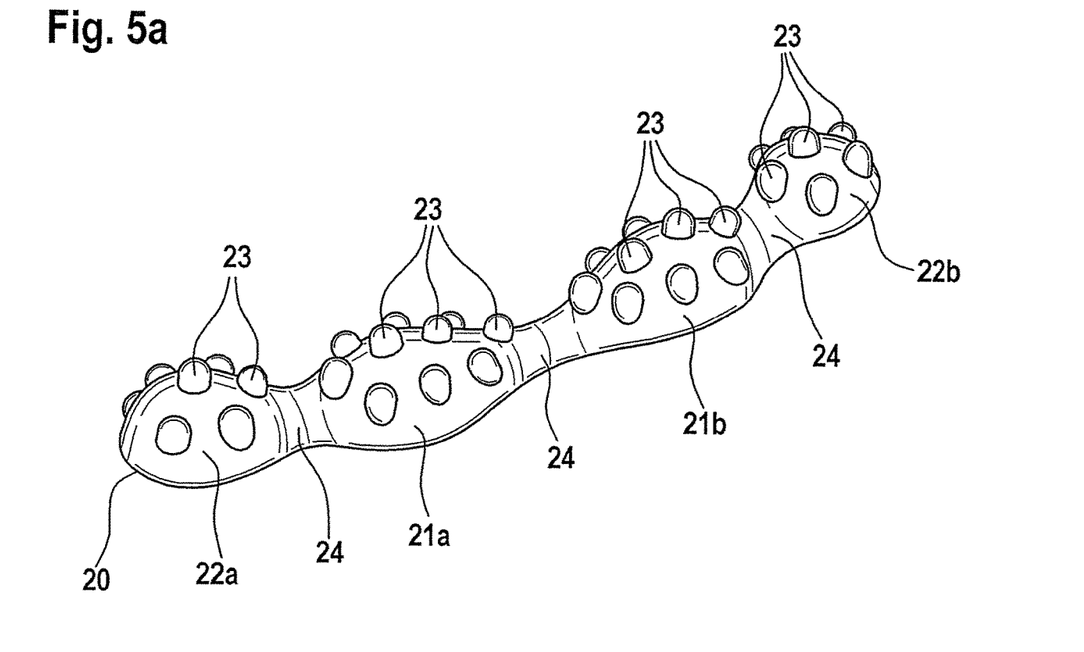
FIG. 5 shows two different embodiments of the patellar tendon bandage according to the invention.
Figure 5B:
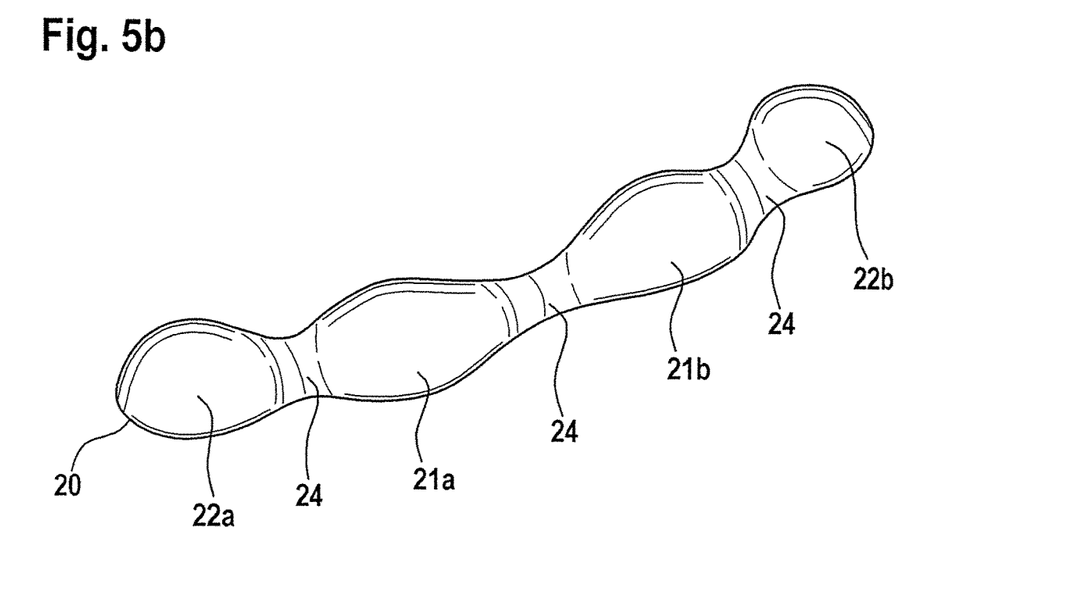

The patellar tendon pressure pad (20) in FIG. 5b, like the pressure pad from FIG. 5a, has two first pressure pad bodies in the form of pressure pad heads (21a, 21b) and two second pressure pad bodies in the form of pressure pad heads (22a, 22b). The total of four pressure pad heads (22a, 21a, 21b, 22b) are connected to one another by means of webs (24), which taper at the center and thus form the one-piece pressure pad (20).

The patellar tendon pressure pads (20) from FIGS. 5a and 5b are suitable, for example, as elements for equipping a patellar tendon bandage. These may be designed, for example, as crocheted orthotic devices with inserted patellar tendon pressure pads (20).

The invention claimed is:
1. A patellar tendon bandage comprising:
a bandage element for circumferentially wrapping about a knee joint with an inner face and an outer face;
two first pressure pad bodies configured to contact the skin of a user and situated on the inner face of the bandage element for building up an infra-patellar pressure;
and two second pressure pad bodies configured to contact the skin of the user on the inner face of the bandage element, the two second pressure pad bodies positioned laterally of the two first pressure pad bodies when wrapped about the knee joint, wherein the two first pressure pad bodies and the two second pressure pad bodies are pressure pad heads inwardly extending from the inner face of the bandage element;

wherein the two second pressure pad bodies are positioned on the inner face of the bandage element for positioning in a lateral region of the knee joint in an applied condition of the patellar tendon bandage and the two second pressure pad bodies act on muscle groups and tendon groups running in the lateral region; and wherein the two first pressure pad bodies and the two second pressure pad bodies are interconnected by webs and form a one-piece pressure pad including four pressure pads and wherein the two first pressure pad bodies and the two second pressure pad bodies are arranged at least approximately on a line parallel to a longitudinal axis of the bandage element.

2. The patellar tendon bandage according to claim 1, wherein the two first pressure pad bodies and/or the two second pressure pad bodies are adjustable in position on the bandage element.

3. The patellar tendon bandage according to claim 1, wherein the two first pressure pad bodies and/or the two second pressure pad bodies are adjustable in height and/or replaceable.

4. The patellar tendon bandage according to claim 1, wherein the two first pressure pad bodies and/or the two second pressure pad bodies have elevations or recesses.

5. The patellar tendon bandage according to claim 1, wherein the bandage element has a front function element and a fixation element, wherein the fixation element is fastened onto at least one end region of the front function element by a first fastening element, so as to be adjustable in length.

6. The patellar tendon bandage according to claim 5, wherein the first fastening element is fastened on the front function element on an outer face of the front function element.

7. The patellar tendon bandage according to claim 5, wherein the first fastening element is fastened on the front function element in a region of one of the two second pressure pad bodies.

8. The patellar tendon bandage according to claim 5, wherein the fixation element is fastened onto first and second end regions of the front function element by first and second fastening elements, respectively, so as to be adjustable in length, wherein the first and second fastening elements are fastened onto the front function element on an outer face of the front function element, and wherein the first fastening element is in a first region proximate to a first second pressure pad body of the two second pressure pad bodies and the second fastening element is in a second region proximate to second pressure pad body of the two second pressure pad bodies each.

9. The patellar tendon bandage according to claim 5, wherein the fixation element has at least one hook-and-loop closure and wherein the first fastening element is a deflecting eye.

10. The patellar tendon bandage according to claim 5, wherein the first fastening element is a fixation belt.

11. The patellar tendon bandage of claim 1, wherein the first two pressure pad bodies and the two second pressure pad bodies are arranged almost on a line and connected to one another by a web.

12. The patellar tendon bandage of claim 1, wherein the two first pressure pad bodies have a first configuration and the two second pressure pad bodies have a second configuration.

13. A patellar tendon bandage comprising:
a bandage element for circumferentially wrapping about a knee joint with an inner face and an outer face;
two first pressure pad bodies configured to contact the skin of a user and situated on the Inner face of the bandage element for building up an infra-patellar pressure; and
two second pressure pad bodies configured to contact the skin of the user on the inner face of the bandage element, the two second pressure pad bodies positioned laterally of the two first pressure pad bodies when wrapped about the knee joint,
wherein the two first pressure pad bodies and the two second pressure pad bodies are pressure pad heads inwardly extending from the inner face of the bandage element;
wherein the two second pressure pad bodies are positioned on the inner face of the bandage element for positioning in a lateral region of the knee joint in an applied condition of the patellar tendon bandage and the two second pressure pad bodies act on muscle groups and tendon groups running In the lateral region; and
wherein the two first pressure pad bodies have an oval shape elongated in a direction parallel to an axis of elongation of the bandage element and the two second pressure pad bodies are approximately circular.

14. The patellar tendon bandage of claim 13, wherein the bandage element is elongated along the axis of elongation and the two first pressure pad bodies and the two second pressure pad bodies are each on a common line parallel to the axis of elongation.

15. The patellar tendon bandage of claim 14, wherein the two first pressure pad bodies are between the two second pressure pad bodies.

16. A patellar tendon bandage comprising:
a bandage element for circumferentially wrapping about a knee joint, the bandage element elongated along an axis of elongation and having an inner face and an outer face;
two first pressure pad bodies configured to contact the skin of a user and situated on the inner face of the bandage element for building up an infra-patellar pressure; and
two second pressure pad bodies configured to contact the skin of the user on the inner face of the bandage element, the two second pressure pad bodies positioned laterally of the two first pressure pad bodies when wrapped about the knee joint,
wherein the two first pressure pad bodies and the two second pressure pad bodies are pressure pad heads inwardly extending from the inner face of the bandage element;
wherein the two first pressure pad bodies and the two second pressure pad bodies are interconnected by webs and form a one-piece pressure pad including four pressure pads and wherein the two first pressure pad bodies and the two second pressure pad bodies are arranged at least approximately on a line parallel to a longitudinal axis of the bandage element; and
wherein the two first pressure pad bodies have an oval shape elongated in a direction parallel to the axis of elongation of the bandage element and the two second pressure pad bodies are approximately circular.

\* \* \* \* \*